United States Patent [19]
Abele et al.

[11] Patent Number: 5,190,541
[45] Date of Patent: Mar. 2, 1993

[54] SURGICAL INSTRUMENT AND METHOD
[75] Inventors: John E. Abele, Concord; Douglas J. Daniels, Mendon; Donald E. Robinson, Hopkinton; Stephen R. Thistle, Scituate, all of Mass.
[73] Assignee: Boston Scientific Corporation, Watertown, Mass.
[21] Appl. No.: 599,144
[22] Filed: Oct. 17, 1990
[51] Int. Cl.$^5$ .............................................. A61B 17/39
[52] U.S. Cl. ........................................ 606/46; 606/48; 606/49; 606/50; 604/35
[58] Field of Search .................. 606/41, 42, 45, 46, 606/48-52, 28; 604/35

[56] References Cited
U.S. PATENT DOCUMENTS

| | | |
|---|---|---|
| 1,932,258 | 10/1933 | Wappler . |
| 2,004,559 | 6/1935 | Wappler et al. . |
| 2,011,169 | 8/1935 | Wappler . |
| 2,052,870 | 9/1936 | Coco . |
| 2,060,724 | 11/1936 | Carroll . |
| 2,676,595 | 4/1954 | Dyekjaer . |
| 3,989,033 | 10/1976 | Halpern et al. . |
| 4,058,126 | 10/1977 | Leveen . |
| 4,201,213 | 5/1980 | Townsed . |
| 4,418,692 | 12/1983 | Guay ........................ 606/45 X |
| 4,593,691 | 6/1986 | Lindstrom et al. . |
| 4,600,007 | 7/1986 | Lahodny et al. . |
| 4,622,966 | 11/1986 | Beard ........................... 606/45 X |
| 4,627,435 | 12/1986 | Hoskin .......................... 606/28 |
| 4,644,951 | 2/1987 | Bays . |
| 4,648,401 | 3/1987 | Mattson . |
| 4,655,215 | 4/1987 | Pike . |
| 4,657,018 | 4/1987 | Hakky . |
| 4,682,598 | 7/1987 | Beraha . |
| 4,804,364 | 7/1986 | Dieras et al. . |
| 4,887,026 | 10/1989 | De Laforcade . |
| 4,887,593 | 12/1989 | Wiley et al. . |
| 4,924,882 | 5/1990 | Donovan . |
| 4,985,030 | 1/1991 | Melzer et al. .................. 606/51 |

FOREIGN PATENT DOCUMENTS

| | | |
|---|---|---|
| 1214357 | 4/1966 | Fed. Rep. of Germany . |
| 2330182 | 6/1973 | Fed. Rep. of Germany . |
| 2415263 | 10/1975 | Fed. Rep. of Germany ........ 606/51 |
| 2903982 | 2/1981 | Fed. Rep. of Germany ........ 606/46 |
| 3707403 | 9/1987 | Fed. Rep. of Germany ........ 606/46 |

OTHER PUBLICATIONS

"The Procedure".
Storz Catalog, "Laparoscopic Cholecystectomy".
"Cholecystectomy", *Laparoscopy-for the General Surgeon*.
FIGS. 1-12.
Cook Catalog.
Rose Bush Pruning Device.
*Primary Examiner*—Lee S. Cohen

*Attorney, Agent, or Firm*—Fish & Richardson

[57] ABSTRACT

A surgical instrument useful for laparoscopic surgery comprising an insulated shaft, a control means and a connection to an electrosurgical radiofrequency power source, its distal end being of general J-hook form having a tissue-engaging ledge, and the shaft supporting a tissue-engaging clamping or cutting member movable toward the ledge in response to the control means so that an artery or other tissue in the pocket of the J-hook can be clamped or cut while radiofrequency current is applied. Instrument constructions disclosed incorporate one or two clamping members and a cutting member arranged such that with actuation, the clamping member(s) engages the ledge before the cutting member, and, by selective actuation of the electrosurgical power source, coagulation current can be applied while clamping an artery or other tissue against the ledge to stop flow of blood, and by further actuation of the control and suitable current to the cutting member, the artery or tissue may be cut. Selector means enable movement of one and prevent movement of one of the members during actuation; bipolar or monopolar energization is employed; the relatively long leg of the J-member has portals. Communicating through a lumen in the shaft for infusion or aspiration of fluid; the distal end surface of the J-hook defines a cutting edge for blunt dissection; and the control means comprises a single actuatable member by actuator rods for sealing clamp and cutting members, while a compression spring associated with the actuating rod of the sealing clamp member compresses when the clamp member is stopped, in clamping action upon the artery or tissue while cutting of tissue thereafter proceeds. A diamond film on tissue-engaging surfaces of a clamp, grasping or cutting surgical instrument improves heat transfer between tissue and instrument.

29 Claims, 5 Drawing Sheets

SURGICAL INSTRUMENT AND METHOD

BACKGROUND OF THE INVENTION

The invention relates to surgical instruments useful in endoscopically guided procedures and in particular in laparoscopic surgery.

Laparoscopic surgery is conducted via the peritoneal cavity by percutaneous insertion of appropriate instruments through the abdominal wall. By manipulation of the instruments while viewing the surgical site through a laparoscope, surgery may be performed on the gallbladder, the kidneys, liver and large bowel, for instance.

Endoscopic surgery in general, and laparoscopic surgery in particular are recognized to have considerable advantages over open surgery because of the avoidance of large incisions and the discomfort, long and expensive hospital stay, and extended period of incapacity required by such incisions. Endoscopic procedures instead employ a few small penetrations of the body, which lessen the patient's discomfort, and reduce the time and expense of the hospital stay and the patient's period of incapacity.

Current methods of laparoscopy require filling the peritoneal cavity with carbon dioxide gas via an inflation device and maintaining inflation pressure. The gas expands the cavity by distending the abdomen, which provides room in which to maneuver the instruments to the selected surgical site. The surgeon uses a variety of instruments to conduct the surgical procedures. For instance, instruments used in isolating the gallbladder from its blood supply and ducts and then removing it from the body via one of the abdominal penetrations include J-form tissue-pulling hooks and retractors of various forms for electrosurgical and laser cutting and cauterizing, forceps, blunt-end dissectors, suction devices, and hollow trocars through which the various instruments are inserted. For the purpose of sealing blood flow in arteries and the like, a device for applying a sealing clip to the artery has been employed, for instance, the Endoclip available from U.S. Surgical, Inc.; typically it is inserted through one of the trocars after other instruments such as J-shaped retractors pull the artery into an exposed position. With the removal and introduction of each instrument through a trocar, carbon dioxide escapes from the peritoneum, and the supply must be replenished to maintain proper inflation, usually by manual methods. Additionally, electrosurgical and other cauterizing devices for laparoscopic or other types of surgery frequently stick to tissue due to the heat generated. One method of cooling has involved water cooling of the devices.

The number of required instruments and their repeated insertion and removal increases the time required for the procedure and its cost. It has been recognized that reduction in the time required for the procedure is highly desirable to enable more procedures to be performed at lower cost and to reduce physician fatigue.

SUMMARY OF THE INVENTION

According to the invention, it is realized that by modifying the J-hook laparoscopic instrument or similar instruments, additional important functions can be performed in endoscopic surgery with significant effect on the efficiency and duration of the surgical procedures, and in some instances improved results can also be obtained.

According to one aspect of the invention, a surgical instrument useful for laparoscopic surgery is provided comprising an insulated shaft extending between proximal and distal ends, the proximal end having a control means and a connection to an electrosurgical radiofrequency power source; the distal end being of general J-hook form having a tissue-engaging ledge on the proximal side of the bottom of the J-hook; and the insulated shaft supporting a tissue-engaging clamping or cutting member movable axially, distally of the instrument toward the ledge in response to the control means whereby tissue such as an artery hooked in the pocket of the J-hook can be engaged on opposite surfaces for clamping or cutting while appropriate radiofrequency current from the power source is applied to the tissue.

Preferred embodiments have one or more of the following features.

The instrument includes at least one clamping member and one cutting member arranged such that upon actuation of the control means the clamping member engages the ledge of the J-hook before the cutting member, whereby, by selective actuation of the electrosurgical power source, coagulation current can first be applied while the clamp clamps an artery or other tissue against the ledge on the inside of the J-hook, thereby to seal the artery or coagulate the tissue to stop bleeding, and thereafter by further actuation of the control and actuation of the power source to provide current to the cutting member, the artery or tissue may be cut by cooperative action of the cutting member and the ledge.

The instrument has two clamp members, one on each side of the cutting member.

The clamp members are movable together towards the ledge by the control means.

The instrument includes selector means which enable movement of at least one of the members while preventing selected movement of one of the members during actuation of the control means.

The instrument is constructed to apply bipolar electrosurgery energization between the J-hook and the movable member or members.

The instrument is constructed to apply monopolar electrosurgery energization to the J-hook and the movable member or members for current flow to a grounding pad associated with the patient.

The relatively long leg of the J-member of the instrument comprises a hollow tube having a plurality of portals, the hollow tube communicating through a lumen in the shaft to a proximal fluid connection for infusion or aspiration of fluid from the surgical site via the portals; preferably the fluid connection has a Y-connection suitable for connection to both infusion means and aspiration means enabling alternate infusion and aspiration through the portals and lumen.

The distally disposed end surface of the J-hook of the instrument is shaped to define a cutting edge for blunt dissection.

The passage through the shaft of the instrument which houses the sealing clamp members and the cutting members is of rounded formation, the clamping members have planar longitudinal inside surfaces parallel to and spaced apart from one another, and the cutter member is disposed therebetween in a manner permitting relative longitudinal motion, the outer longitudinal surfaces of the clamp members being of matched configuration to the corresponding curved walls of the passage for guided movement; preferably, the passage is of oval form and, as viewed in transverse cross-section, the clamp members extend along the long sides of said oval.

The control means of the instrument comprises a single actuatable member constructed to apply axial motion to actuator rods associated with the sealing clamp and cutting members, a compression spring associated with the actuating rod(s) of the sealing clamp member(s) constructed to compress while the sealing clamp member is stopped in clamping action upon the artery or tissue while further motion of the actuatable member causes the cutter to cut the tissue, preferably, means are provided to adjustably vary the preloading of the spring to enable adjustment of the pressure with which the tissue is clamped before cutting or the distance of offset between the ends of the clamp and the cutting member.

Finally, a diamond film or layer on tissue-engaging surfaces of a clamp, grasping, or cutting surgical instrument can improve heat transfer between tissue and the instrument. This can e.g. reduce sticking of tissues to the instrument. This feature applies both to laparoscopic surgical instruments and instruments for other types of surgery.

Other features and advantages of the invention will become apparent from the following detailed description and from the claims.

DESCRIPTION OF THE PREFERRED EMBODIMENTS

STRUCTURE AND OPERATION

Figure 1:
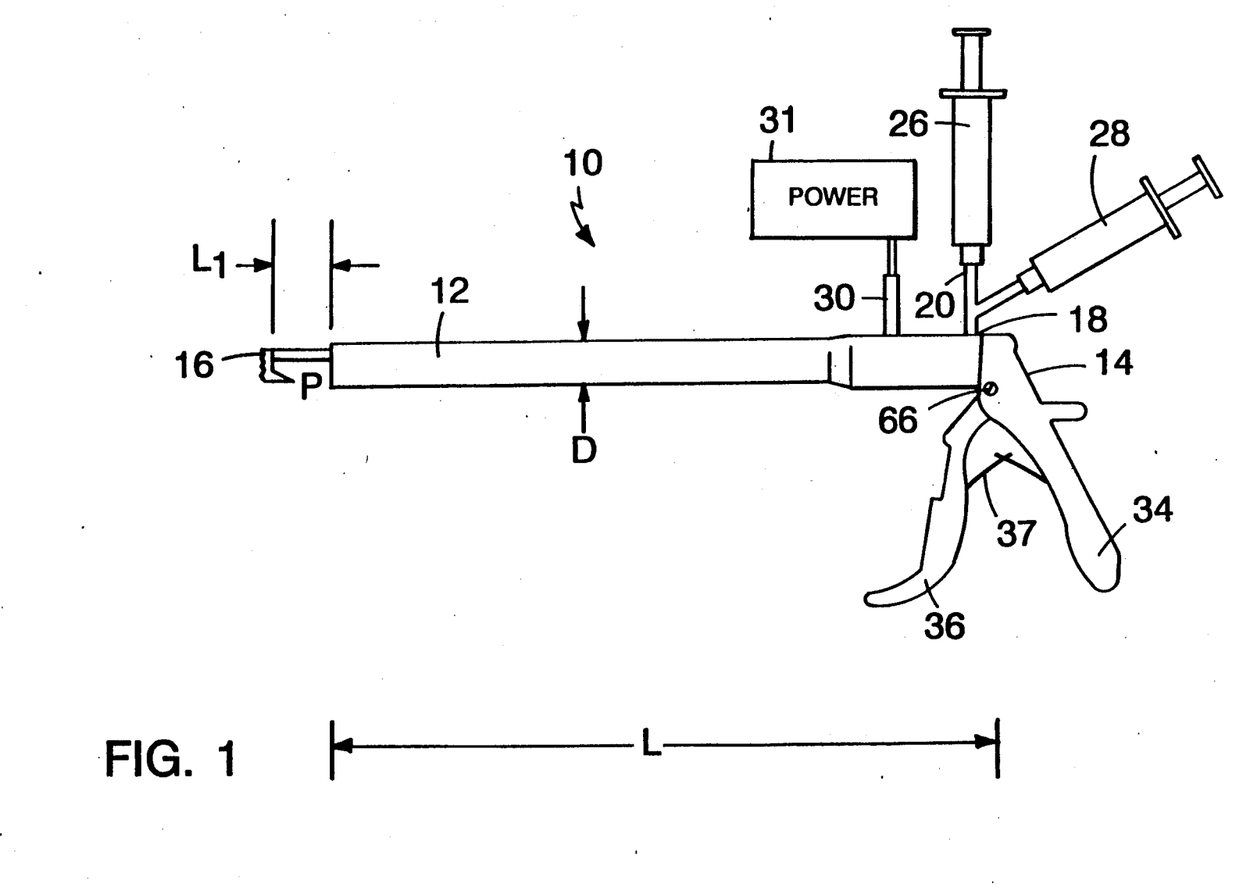
FIG. 1 is a side view of a preferred multipurpose laparoscopic surgical instrument according to the invention.
Figures 6, 6A:
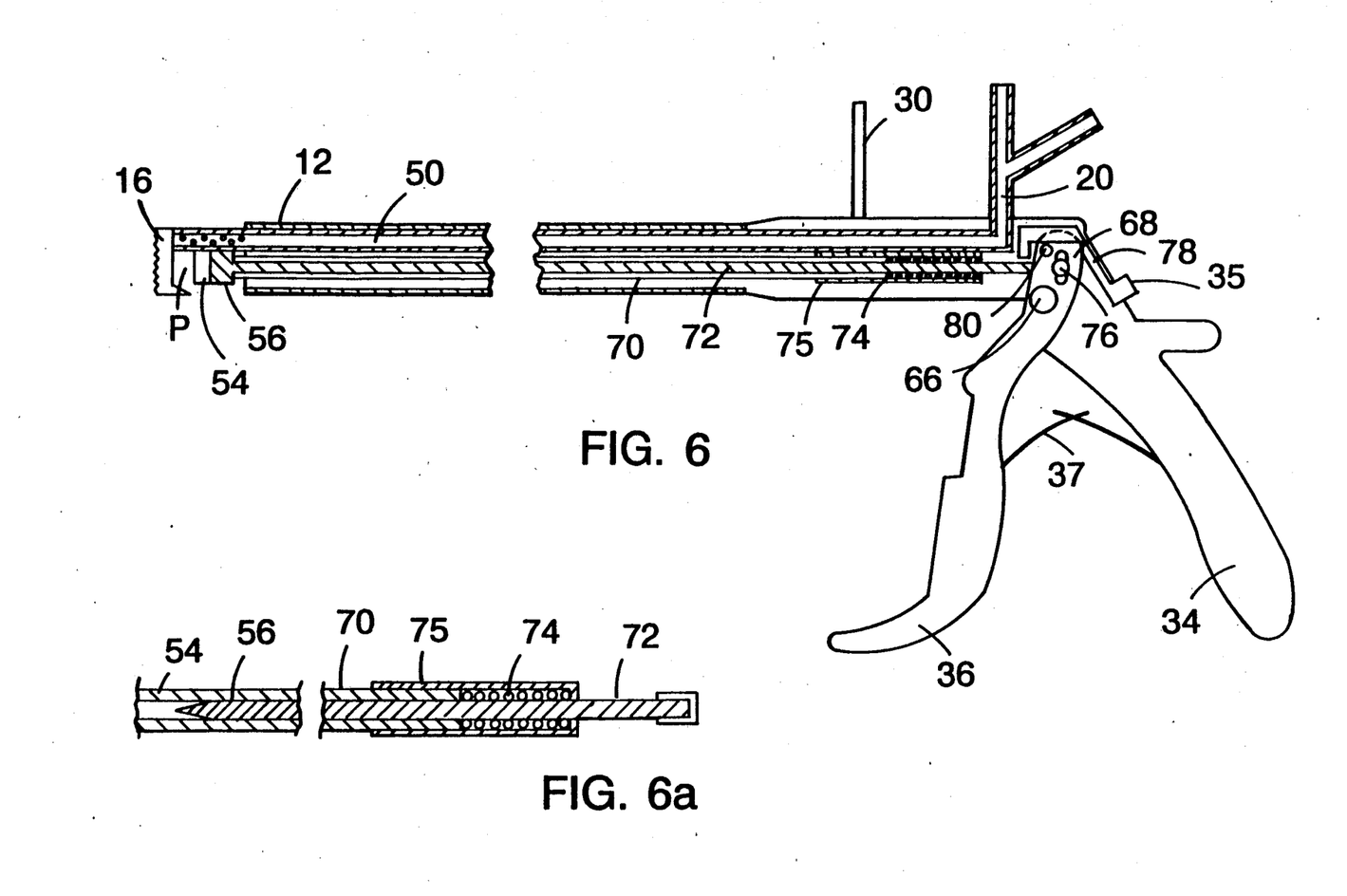
FIG. 6 is an enlarged side view, partly in cross-section showing the operating mechanism of the instrument.
FIG. 6a is a plan view of the instrument of FIG. 6.

Referring to FIGS. 1 and 6 the main body of the multipurpose laparoscopic surgical instrument 10 comprises a rigid insulated shaft 12 which has a control section 14 at its proximal end and a J-hook formation 16 at its distal end. The instrument is most preferably made of sterilizable stainless steel, and the shaft is approximately 32 cm in length, L, and 4.8 mm in diameter, D, constructed for insertion through a trocar to a surgical site within the body. The insulation may be provided by a fluorocarbon coating such as Teflon TM from du-Pont.

The control section 14 has a fixed handle part 34 and a movable trigger part 36. Also, at the proximal end, the shaft 12 has a single lumen suction/irrigation portal 18 from which extends a Y-connector 20. One branch of the Y-connector 20 is shown connected to a suction tube, which leads to a suction syringe 26. The other branch of the Y-connector 20 is shown connected to an irrigation tube, which leads to an irrigation syringe 28. This portion of the instrument provides selectable suction and irrigation through lumen 50 which extends through shaft 12 to the distal end of the instrument. In addition, an electrical connector 30 extends from the shaft 12 for connection to an electrosurgical radiofrequency power source 31 which is associated with a control, such as a foot switch.

Figure 2:
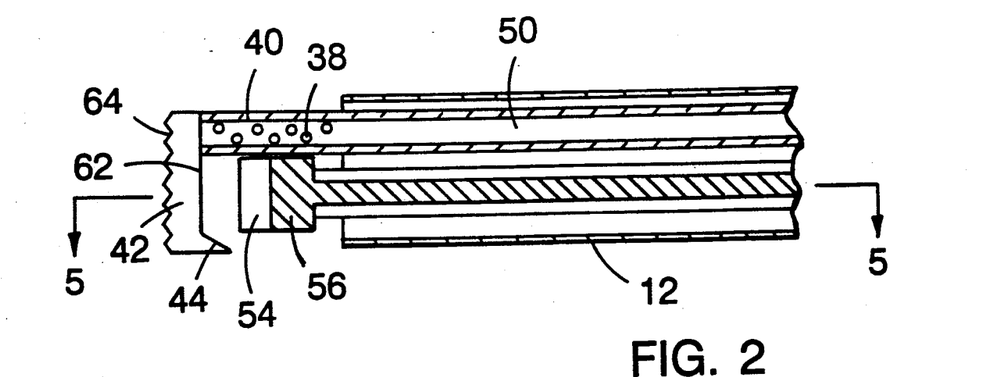
FIG. 2 is an enlarged longitudinal cross-section view of the distal end of the instrument.
Figures 3, 4:
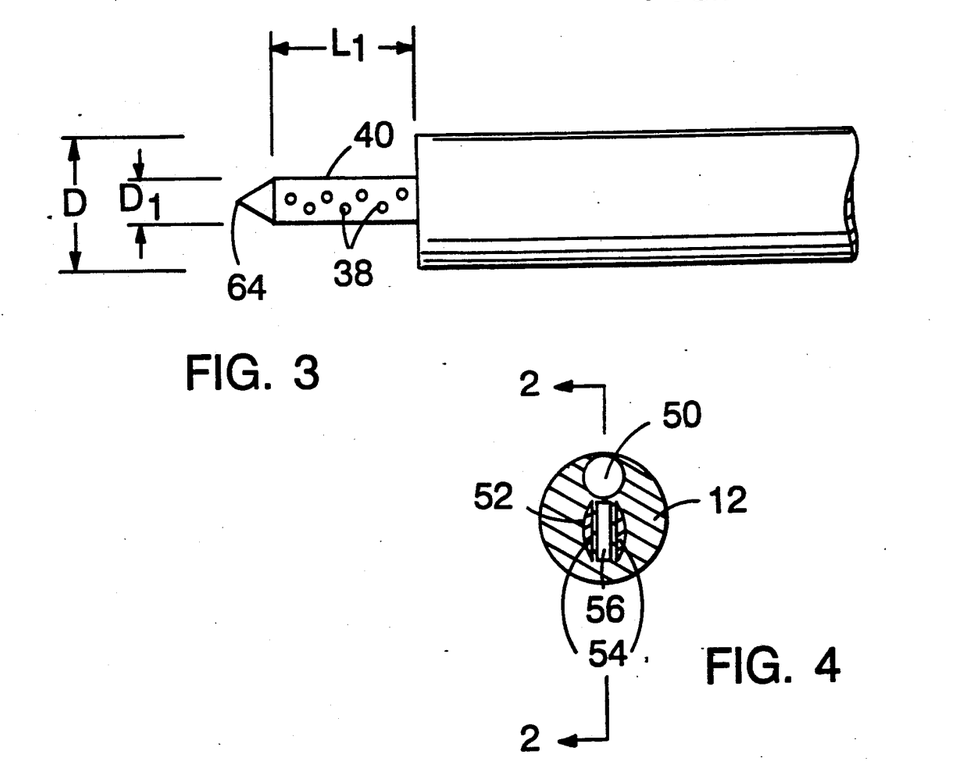
FIG. 3 is an enlarged plan view of the distal end of the instrument.
FIG. 4 is an enlarged cross-sectional view taken on line 4—4 of FIG. 1.

At the distal end, the J-hook formation 16 is formed by a hollow tubular leg 40 of diameter $D_1$, e.g. 2 mm, extending $L_1$, e.g. 6 mm, beyond the distal end of shaft 12, and by cross-member 42 joined to the distal end of leg 40. Cross-member 42 defines a ledge 62 on its proximal side (inside surface of the J) and a serrated cutting edge 64 on its distal side, see FIG. 2. The serrated edge 64 as seen in plan in FIG. 3 tapers to a cutting edge suitable for blunt dissection of tissues by end-wise, distal movement of the instrument. The hollow leg 40 of the J-hook 16 has a plurality of suction/irrigation portals 38 communicating with lumen 50. The J-hook 16 has returning tip 44 on the free end of the cross-member 42. Tip 44, points proximally for hooking purposes, see FIG. 2. The thickness of the cross-member 42 and the hook 44, in the direction normal to the plane of FIG. 2 is 2 mm, corresponding to the diameter of leg 40.

The rigid insulated shaft 12 conducts electrosurgery power via metal leg 40 to the cross-member 42. Parallel to the suction/irrigation lumen 50, a longitudinal passage 52 of oval cross section extends through the shaft 12. This passage houses two sealing-clamp bars 54 and an electrosurgical cutting knife 56. The distal ends of the sealing/cutting bars are flat and constructed to press against matching anvil surfaces provided by the cross-member 42, see FIG. 5. The outer longitudinal side of each sealing clamp 54 is crescent shaped to conform to the corresponding inside surface of oval passage 52, while the inside longitudinal surface of the clamps are planar, parallel and spaced apart. The cutting knife 56 lies in the space between the two clamps 54. In the distal region the knife extends the full dimension of oval passage 52, as shown in the cross section of FIG. 4. A knife actuating shaft 72 extends proximally from knife 56 to the control section, to transmit axial movement to the knife. In one embodiment, the exposed anvil surfaces and the end surfaces of the sealing clamps 54 and the knife 56 have a diamond film for purposes of heat transfer in preferred embodiments. Such films may be produced by vapor deposition method such as employed by General Electric Superabrasives Inc., see for instance Fisher, "Science Newsfront", *Popular Science*, pp. 25–26, (Oct. 1990), and Anthony, Banholzer and Fleischer publications and patents on this subject, herein incorporated by reference.

In the first preferred embodiment, a pin 76 is located above the pivot 66 on the movable trigger part 36 and pivotally connects to shaft 72. The knife blade 56 is thereby driven axially by shaft 72. Likewise actuating shafts 70, FIG. 6a, for the two sealing clamps 54 are directly driven by shaft 72. A yieldable compression spring 74 is captured in spring retention sleeve 75, which is fixed to shaft 72 and retains the proximal ends of shafts 70. Thus the compression spring is interposed in the drive linkage for each clamp, such that when the sealing clamp bottoms on its respective anvil surface of the ledge, or upon an artery, vein, duct or tissue interposed between the anvil and the sealing clamp, the trigger 36 is capable of further actuating motion, applying increasing pressure on the body-part, but with no further substantial motion of the sealing clamps.

The respective actuating shafts for the sealing clamps are dimensioned such that when the trigger 36 is in released position under the influence of its return spring 37, the clamps are entirely withdrawn into hollow shaft 12, and the tissue receiving pocket P formed between the inside ledge 62 of the J-hook and the end of shaft 12 is entirely open to receive an artery, vein, duct or tissue to be retracted or otherwise acted upon by the instrument. The actuating shaft 72 for the knife blade is sized in length to position the blade even further proximally within hollow shaft 12 in the manner that during actuation, the sealing clamp can clamp the tissue fully before the blade has contact with the tissue. This can permit selective clamping and subsequent release, or clamping and sealing by application of coagulating current without cutting if desired, or cutting may be actuated by increased squeeze on the trigger only after it is observed that desired sealing action of the artery, vein or duct under the sealing clamp has occurred.

(Those familiar with gardening may realize the similarity of this action to the action of known rose bush pruning devices which incorporate clamping and cutting device to clamp a branch securely before the blade engages the branch for cutting.)

A safety latch device 35, having a pivot 78 and disposed to engage a stop pin 80, is associated with trigger 36. When set, the device 35 limits the motion of trigger 36 to that required for clamping, and when released, it permits full travel to enable successive clamping and cutting, see FIG. 6.

For the preferred bipolar electrosurgical operation the tissue-engaging surfaces of the cross member are preferably associated with the positive terminal of the rf electrosurgery power supply and the sealing/clamping bars and the knife are negative. For such embodiments the interior of the oval passage 52 is insulated or other means are employed to electrically isolate the respective parts of the instrument and the connecting terminal 30 is constructed to provide bipolar energization. In the present embodiment it is contemplated that during cutting, the current will be selected to employ the field-concentrating effect of the knife to cause cutting at the knife, while any current at the clamp members will be at such a low current density as to be insufficient to cause cutting. In this form the instrument can be used for monopolar operation in the conventional manner when the clamp and cutting members are withdrawn, by use of a conventional grounding pad associated with the patient. In an alternative preferred bipolar construction, the clamp members 54 and the knife 56 are positive and the cross-member 42 is grounded. If desired, the clamp members and their actuators can then be electrically isolated from the knife member and its actuator, to enable distinctly different currents (e.g. coagulating and cutting currents respectively) to be applied to the clamp members and knife, when desired.

Figure 5A:
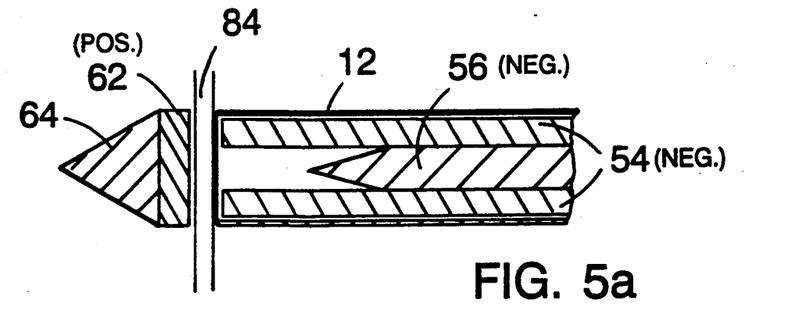
FIGS. 5a, 5b and 5c are a series of views demonstrating the operation of the instrument of FIG. 1 at the surgical site.
Figure 5B:
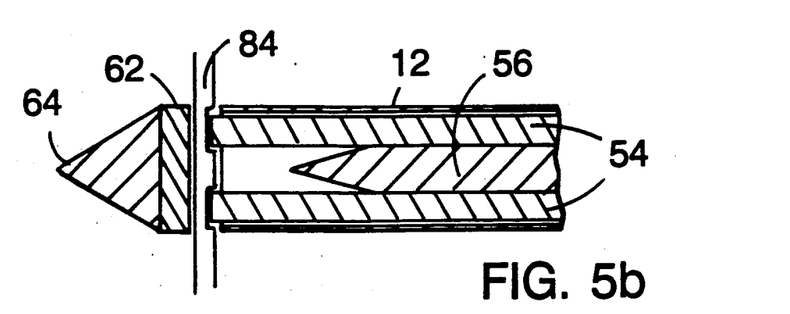
Figure 5C:
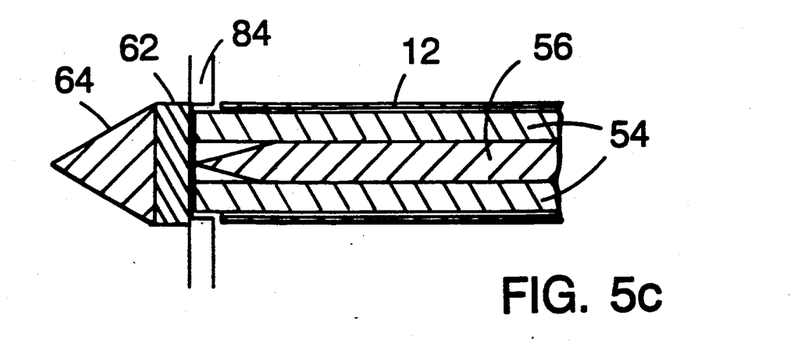

FIG. 5 shows the operation of the distal end of the instrument. By taking the section at line 5—5 in FIG. 2, the returning tip 44 of the J-hook 16 is not shown to enable the sealing clamps and blade to be shown more fully.

In FIG. 5a a blood vessel 84 has been hooked into the pocket P of the J-hook 16 after being separated from the surrounding tissue by blunt dissection using the novel distal serrated edge 64 of this J-hook instrument, or by other techniques. In hooking the tissue the instrument has been used in manner normal to J-hooks. The blood vessel 84 lies perpendicular to the two sealing clamps 54 and the cutting knife 56 and cross-wise over the blunt ledge 62 or anvil of the cross-member 42 of the J-hook 16.

In FIG. 5b, by partially pulling the trigger, the clamps 54 have been moved toward the anvil surface of ledge 62 to clamp the vessel in two places. If it is only wished to temporarily hold the vessel during the surgical procedure, the control trigger may subsequently be released to release the vessel, unimpaired. In this case the instrument has acted as a forceps. If it is wished to seal the vessel, electrosurgery power is applied at coagulating rf current levels when the clamps grip the blood vessel. As a result the blood vessel 64 is cauterized and sealed at the positions of the clamps by the bipolar radiofrequency current that passes through the tissue, so that blood no longer can flow through the vessel.

In FIG. 5c, after releasing the safety device 35, further squeezing of the trigger 36 causes the cutting knife 56 to move through the blood vessel 84 between the sealed regions, thus severing the blood vessel 84, as desired. While it is possible to employ knife edge cutting, or slicing, in the preferred form of the present embodiment electrosurgical current of cutting quality (or a blend of cutting and coagulating current) is applied between the leading part of the knife and the opposed portion of th ledge 62 of cross-member 42.

In the embodiment in which the tissue-engaging surfaces (i.e., the anvil surface of the cross-member 42 and the distal ends of the clamps 54 and the knife 56) are coated with a diamond film, heat transfer between those surfaces and the blood vessel 84 can be improved to reduce sticking of the blood vessel 84 to those surfaces.

Referring to FIG. 6 the operation of the internal mechanism for the steps of FIG. 5 will be described. The surgeon draws the movable trigger 36 of the control 32 proximally toward the fixed handle 34. The movable trigger 36 attaches to the fixed part 34 at a pivot point 66, but a small upper extension 68 of the movable part 36 extends beyond the pivot 66 and includes the pin 76 and slot arrangement, as mentioned above. As the surgeon draws the movable part 36 proximally, the upper portion 68 with the pin 76 moves distally, moving the proximal end of actuating shaft, and therewith, shafts 70. The distal motion of the outer shafts 70 causes the clamps 54 to move distally, while the distal motion of the inner shaft 72 causes the cutting knife 56 to move distally. The compression spring 74 associated with the actuating shaft for each clamp 54 moves with the assembly. When the clamps 54 can no longer move distally due to engagement with the blood vessel 64 and clamping of it against the anvil, the compression of the spring 74 attached to the clamps 54 allows the continued motion of the cutting knife 56. The trigger return spring 37, assures the return of the clamps and knife distally upon release of the trigger. A selector mechanism, such as the safety device 35 shown in FIG. 6, can be adjusted by the surgeon to lock the movable cutting knife 56, such that distance of travel of the trigger is limited so that only clamping occurs when the trigger is squeezed. In the present embodiment, the trigger 36 advances until the latch 35 comes into contact with the stop pin 80. Depressing the latch 35 raises its end opposite the pivot pin 78 (i.e., the end that contacts the stop pin 80). Such release of the latch allows the trigger 36 to continue the stroke.

In another preferred embodiment the spring-retaining, clamp-supporting sleeve 75 is threaded to the actuation rod 72 for the cutting blade. By rotating the sleeve on the threads the position of the distal ends of the sealing clamp members can be varied relative to the cutting blade. This can be employed to vary the relationship of clamping to cutting, relative to actuation motion of the trigger, and can as well be used to vary the clamping pressure attained prior to cutting.

As mentioned above, in addition to the clamping and cutting functions, the J-hook 16 of the instrument may also be used for simple hooking, and its serrated edge 64 permits its use for blunt dissection. Furthermore, the portals 38 and lumen 50, together with the attached suction and irrigation syringes 26 and 28, permit controlled alternate suction and irrigation of the surgical area through the multiple suction/irrigation portals 38 in the hollow tubular leg 40 of the J-hook 16. Thus during the surgery e.g. after an artery is hooked but before sealing and cutting, blood in the field may be aspirated, saline introduced for washing, and further aspiration performed for cleaning th field prior to the electrosurgery. Similarly, after cutting an artery, the instrument can again be used for an aspiration, infusion sequence. This suction/irrigation feature thus further reduces the usual number of instrument interchanges required during surgery, minimizing the need for interruptions in the procedure and loss of inflation gas.

Figure 7:
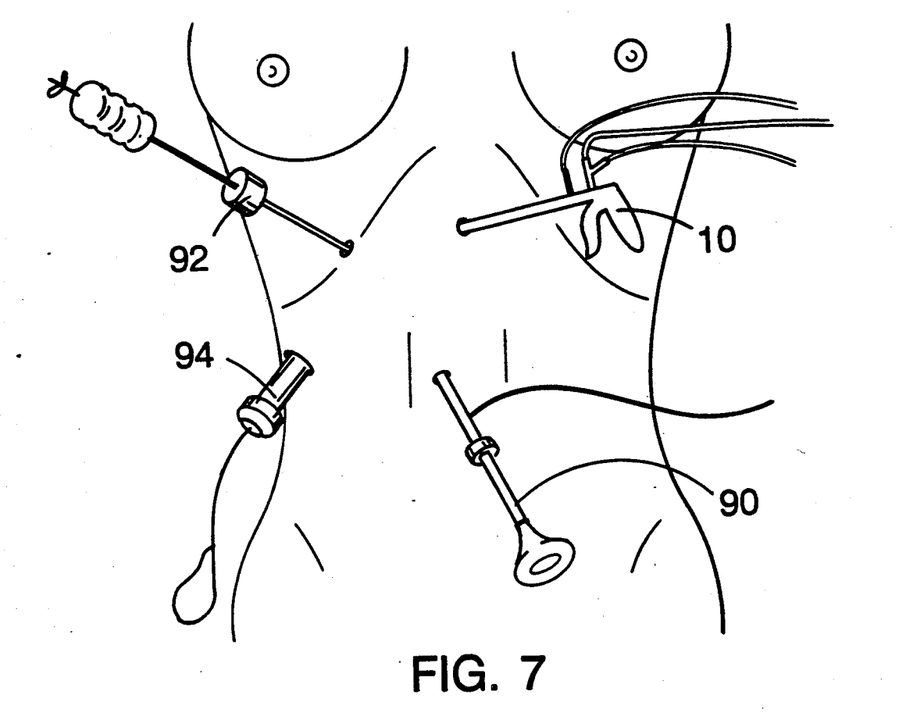
FIG. 7 is a view depicting a patient undergoing laparoscopic surgery.

For further understanding of the use of the instrument, we refer to FIG. 7. A laparoscope 90 is introduced through a 10 mm trocar into the peritoneal cavity through the upper part of the patient's umbilicus and directed toward the liver. The peritoneal cavity is then inflated with carbon dioxide gas. A 5 mm trocar is inserted near the gallbladder fundus and a forceps 92 is introduced and used to grasp the fundus. A 5 mm trocar is inserted into the mid-clavicle area and the surgical instrument 10 of the present application is introduced through it. A 10 mm trocar is inserted into the lower right quadrant of the abdomen and a grasping instrument 94 is introduced through this trocar. The surgeon then operates on the patient.

OTHER EMBODIMENTS

In another preferred embodiment a selector mechanism is incorporated in the instrument to enable selection of which one of the active elements or which number of the elements will move upon actuation of the control. Depending upon the particular selector mechanism and its setting, it is readily possible for the surgeon to lock the movable cutting blade, so that only clamping occurs upon squeeze of the handle, or for the surgeon to select only the cutting blade for movement, or to select one or the other of the clamps to move. In another preferred embodiment multiple triggers are provided for the respective elements, and appropriate safety latches can be included. In other preferred embodiments, only a single clamp is provided, with and without a cutting blade, and in another preferred embodiment only a cutting blade is provided.

Other embodiments of the invention include various combinations of the coagulation, cutting and suction/irrigation functions. In these embodiments, too, the instrument can have a knife, but no clamps; or an instrument can comprise a J-hook having a serrated edge for blunt dissection without including either the knife or the clamps and either with or without suction/irrigation. There can be one clamp used alone or located to one side of the cutting knife. Multiple triggers for the various movable elements and safety catches can be again included. Other than J-hooks per se, equivalents forms can be employed to perform the functions described.

These and numerous other embodiments will be within the spirit and scope of the claims.

We claim:

1. A surgical instrument useful for laparoscopic surgery comprising an insulated shaft extending between proximal and distal ends,
    said proximal end having a control means for controlling clamping or cutting by the instrument and a connection to an electrosurgical radiofrequency power source;
    said insulated shaft having conductor means serving to conduct radiofrequency power from said connection to the distal end of the instrument;
    said distal end being of general J-hook form defining a tissue-receiving pocket, the J-hook having a bottom with a proximal side which defines a tissue-engaging ledge;
    said insulated shaft supporting tissue-engaging clamping or cutting members, said members movable axially, distally of the instrument toward said ledge in response to said control means for successively engaging said tissue by a first of said members at a first point along said ledge and subsequently by a second of said members at another point spaced along said ledge from the first engaged point, whereby tissue such as an artery or other tissue hooked in the pocket of said J-hook can be engaged on opposite surfaces for clamping or cutting while appropriate radiofrequency current from said power source is applied to said tissue.

2. A surgical instrument useful for laparoscopic surgery comprising an insulated shaft extending between proximal and distal ends,
    said proximal end having a control means for controlling clamping or cutting by the instrument and a connection to an electrosurgical radiofrequency power source;
    said insulated shaft having conductor means serving to conduct radiofrequency power from said connection to the distal end of the instrument;
    said distal end being of general J-hook form defining a tissue-receiving pocket, the J-hook having a bottom with a proximal side which defines a tissue-engaging ledge;
    said insulated shaft supporting at leas one tissue-engaging clamping member and at least one tissue engaging cutting member each movable axially, distally of the instrument toward said ledge in response to said control means whereby tissue such as an artery or other tissue hooked in the pocket of said J-hook can be engaged on opposite surfaces for clamping or cutting while appropriate radiofrequency current from said power source is applied to said tissue.

3. The instrument of claim 2 constructed and arranged such that upon actuation of said control means said clamping member engages said ledge of said J-hook before said cutting member, whereby, by selective actuation of said electrosurgical power source, coagulation current can be applied while said clamp clamps said artery or other tissue against the ledge on the inside of the J-hook, thereby to seal said artery or coagulate said tissue to stop bleeding.

4. The instrument of claim 3 in which said control means is constructed and arranged to enable further actuation of said control to cut said artery or tissue by cooperative action of said cutting member and said ledge.

5. The instrument of claim 4 wherein said connection to said power source is connected to provide current to said cutting member, whereby the artery or tissue may be cut electrosurgically.

6. The instrument of claim 2 wherein two clamp members are provided, one on each side of said cutting member.

7. The instrument of claim 3, 4 or 5 wherein two clamp members are provided, one on each side of said cutting member.

8. The instrument of claim 6 wherein said clamp members are movable together toward said ledge by said control means.

9. The instrument of claim 7 wherein said clamp members are movable together toward said ledge by said control means.

10. The instrument of claim 2, 3, 4, 5, 6 or 8 including selector means enabling movement of at least one of said members while preventing selected movement of one of said members during actuation of said control means.

11. The instrument of claim 1, 2, 3, 4, 5, 6 or 8 wherein said connection and said conductor means are constructed to apply bipolar electrosurgery energization between said J-hook and said movable members.

12. The instrument of claim 11 wherein said members are electrically isolated from one another, said conductor means constructed to enable cutting current to be applied to one of said members without applying cutting current to the other of said members.

13. The instrument of claim 1, 2, 3, 4, 5, 6 or 8 wherein said connection and said conductor means are constructed to apply monopolar electrosurgery energization to said J-hook and said movable members for current flow to a grounding pad associated with the patient.

14. The instrument of claim 1, 2, 3, 4, 5 or 8 wherein said shaft comprises a hollow tube and a distal extremity of said tube has a plurality of portals, said hollow tube communicating to a proximal fluid connection for infusion or aspiration of fluid from a surgical site via the portals.

15. The instrument of claim 14 wherein said fluid connection has a Y-connection suitable for connection to both infusion means and aspiration means enabling infusion and aspiration through said portals and said hollow tube.

16. The instrument of claim 1, 2, 3, 4, 5, 6 or 8 wherein a distally disposed end surface of said J-hook is shaped to define a cutting edge for blunt dissection.

17. The instrument of claim 1, 2, 3, 4, 5, 6 or 8 wherein said shaft comprises a hollow tube and a distal extremity of said tube has a plurality of portals, said hollow tube communicating to a fluid connection for infusion or aspiration of fluid from a surgical site via the portals and wherein a distally disposed end surface of said J-hook is shaped to define a cutting edge for blunt dissection.

18. The instrument of claim 6 or 7 wherein said shaft includes a passage that is of rounded formation, said clamping members have planar longitudinal inside surfaces parallel to and spaced apart from one another, and said cutting member is disposed therebetween in a manner permitting relatively longitudinal motion, said clamp members having outer longitudinal surfaces configured to match corresponding curved walls of said passage for guided movement.

19. The instrument of claim 18 where said passage is of oval form having two opposed long sides and, as viewed in transverse cross-section, said outer longitudinal surfaces of said clamping members extend along the long sides of said oval.

20. The instrument of claim 2, 3 or 4 wherein said control means comprises a single actuatable member and respective actuator rods connected to said clamping member and said cutting member, said actuatable member, constructed to apply axial motion to said actuator rods to actuate said clamping and cutting members, a compression spring connected to the actuating rod of said clamping member constructed to compress while said clamping member is stopped in clamping action upon said artery or tissue while further motion of said actuatable member causes said cutting member to cut said tissue.

21. The instrument of claim 20 wherein means are constructed to adjustably vary the preloading of said spring to enable adjustment of the pressure with which said tissue is clamped before cutting.

22. The instrument of claim 1, 2, 3, 4, 5 or 6 in which a tissue-engaging surface of at least one of said members comprises a coated diamond film outer layer enabling improved heat transfer between said tissue and said member.

23. The instrument of claim 22 wherein said tissue-engaging member the surface of which comprises said diamond-film is electrically conductive and is connected to said conductor means for producing a flow of radiofrequency current for cauterizing, coagulating or cutting tissue, said diamond film layer serving to conduct heat from said tissue to said instrument for cooling said tissue.

24. A surgical instrument useful for laparoscopic surgery comprising an insulated shaft extending between proximal and distal ends,
said proximal end having a control means for controlling clamping or cutting by the instrument and a connection to an electrosurgical radiofrequency power source; and
said insulated shaft supporting a tissue engaging clamping or cutting member near the distal end of said instrument moveable to effect clamping or cutting in response to said control means, and further
said insulated shaft having conductor means serving to conduct radiofrequency power from said connection to the distal end of the instrument;
said distal end being of general J-hook form defining a tissue-receiving pocket, the J-hook form having a bottom with a proximal side which defines a tissue-engaging ledge, said shaft comprises a hollow tube and a distal extremity of said tube has a plurality of portals, said hollow tube communicating to a proximal fluid connection for infusion or aspiration of fluid from a surgical site via the portals.

25. A surgical instrument useful for laparoscopic surgery comprising an insulated shaft extending between proximal and distal ends,
said proximal end having a control means for controlling clamping or cutting by the instrument and a connection to an electrosurgical radiofrequency power source; and said insulated shaft supporting a tissue engaging clamping or cutting member near the distal end of said instrument moveable to effect clamping or cutting in response to said control means, and further said insulated shaft having conductor means serving to conduct radiofrequency power from said connection to the distal end of the instrument;

said distal end being of general J-hook form defining a tissue-receiving pocket, the J-hook having a bottom with a proximal side which defines a tissue-engaging ledge, and wherein a distally disposed end surface of said J-hook is shaped to define a cutting edge for blunt dissection.

26. A surgical instrument useful for laparoscopic surgery comprising an insulated shaft extending between proximal and distal ends, said proximal end having a control means for controlling clamping or cutting by the instrument and a connection to an electrosurgical radiofrequency power source; and said insulated shaft supporting a tissue engaging clamping or cutting member near the distal end of said instrument moveable to effect clamping or cutting in response to said control means, and further said insulated shaft having conductor means serving to conduct radiofrequency power from said connection to the distal end of the instrument;

said distal end being of general J-hook form defining a tissue-receiving pocket, the J-hook having a bottom with a proximal side which defines a tissue-engaging ledge, said shaft comprising a hollow tube and a distal extremity of said tube has a plurality of portals, said hollow tube communicating to a proximal fluid connection for infusion or aspiration of fluid from a surgical site via the portals, and wherein a distally disposed end surface of said J-hook is shaped to define a cutting edge for blunt dissection.

27. A surgical instrument for laparoscopic electrosurgery having an elongated shaft extending between proximal and distal ends, said proximal end having a connection to an electrosurgical radiofrequency power source, said shaft having insulated conductor means serving to conduct radiofrequency power from said connection to the distal end of the instrument, at said distal end a tissue-engaging member has a tissue-engaging surface comprising a coated diamond film outer layer, said diamond film layer enabling improved heat transfer of heat generated during electrosurgery between said tissue and said tissue-engaging member.

28. The instrument of claim 27 wherein said member is electrically conductive and is connected to said conductor means for producing a flow of radiofrequency current for cauterizing, coagulating or cutting tissue, said diamond film layer serving to conduct heat from said tissue to said instrument for cooling said tissue.

29. A surgical instrument useful for laparoscopic surgery comprising an insulated shaft extending between proximal and distal ends, said proximal end having a control means for controlling clamping or cutting by the instrument and a connection to an electrosurgical radiofrequency power source;

said insulated shaft having conductor means serving to conduct radiofrequency power from said connection to the distal end of the instrument;

said distal end being of general J-hook form defining a tissue-receiving pocket, the J-hook having a bottom with a proximal side which defines a tissue-engaging ledge;

said insulated shaft supporting a tissue-engaging clamping or cutting member movable axially, distally of the instrument toward said ledge in response to said control means whereby tissue such as an artery or other tissue hooked in the pocket of said J-hook can be engaged on opposite surfaces for clamping or cutting while appropriate radiofrequency current from said power source is applied to said tissue;

wherein said shaft comprises a hollow tube, and a distal extremity of said tube has a plurality of portals, said hollow tube communicating to a proximal fluid connection for infusion or aspiration of fluid from a surgical site via the portals;

said fluid connection having a Y-connection suitable for connection to both infusion means and aspiration means enabling alternate infusion and aspiration through said portals.

* * * * *